US00PP19077P2

(12) United States Plant Patent
Hartmann

(10) Patent No.: US PP19,077 P2
(45) Date of Patent: Aug. 5, 2008

(54) BLUEBERRY PLANT NAMED 'HX'

(50) Latin Name: *Vaccinium*
Varietal Denomination: HX

(75) Inventor: Patrick J. Hartmann, Grand Junction, MI (US)

(73) Assignee: Hartmann's Plant Company, Grand Junction, MI (US)

( * ) Notice: Subject to any disclaimer, the term of this patent is extended or adjusted under 35 U.S.C. 154(b) by 0 days.

(21) Appl. No.: 11/805,787

(22) Filed: May 24, 2007

(51) Int. Cl.
*A01H 5/00* (2006.01)

(52) U.S. Cl. ..... Plt./157

(58) Field of Classification Search ..... Plt./157
See application file for complete search history.

*Primary Examiner*—Annette H Para
(74) *Attorney, Agent, or Firm*—Flynn, Thiel, Boutell & Tanis, P.C.

(57) ABSTRACT

A new and distinct low-chill blueberry (*Vaccinium*) variety 'HX'. The parent of 'HX' is 'Avonblue' (unpatented) an interspecific hybrid of several species. 'HX' is (a) free flowering without the use of growth regulating chemicals, (b) has the lowest chilling requirement on all commercial cultivar, (c) has the earliest fruiting of all commercial cultivar, (d) is resistant to *phytophthora cinnamomii* and (e) its fruits ripen uniformly.

3 Drawing Sheets

*Vaccinium.*

BACKGROUND OF THE INVENTION

The present invention relates to a blueberry Variety, 'HX' Blueberry plant.

The closest known variety is its parent 'Avonblue' (unpatented) an interspecific hybrid.

The variety 'HX', was developed by Hartmann's Plant Company.

*Vaccinium* hybrid 'HX' was derived from an open pollinated seed tested as E-2. The parent of 'HX' is Avonblue (non-patented), an interspecific hybrid of corymbosum, ashei, darrowi and australe. Plants of 'HX' were hybridized at Hartmann's Blueberry Lane Plantation, located in Earleton, Fla. The hybridization took place in 1973 and testing resumed of the variety from that date until the present.

SUMMARY OF THE VARIETY

The following is a summary of the description of the new and distinct variety of blueberry, its flower, fruit and foliage based on observation of specimen grown in Earleton, Fla.

'HX' is free flowering without the use of growth regulating chemicals. 'HX' is a multi-stemmed, erect shrub. Branches are slightly spreading to 3 feet (1 meter). It has a lower chilling requirement than that of all commercial cultivars. It has the earliest fruiting of all commercial cultivar. It is resistant to phytophthora cinnamomii. The fruits ripen uniformly.

Fruit quality is firm with a small picking scar. The fruit is suitable for fresh markets, but cannot be stored for long periods of time. Storage for 10 days at 35 degrees F. (1.5 degrees C.). First fruits ripen earliest of all cultivar in Earleton, Fla. In the year 1988, fruit was first harvested on March 2 in Earleton, Fla. In subsequent years the fruit ripened within the beginning of March and within 10 days or less.

ASEXUALLY REPRODUCTION OF THE VARIETY

'HX' was asexually propagated in a cultivated area of Earleton, Fla. in 1973 utilizing soft wood cuttings. The plants so propagated have shown that the unique features of this new *Vaccinium* plant are stable and reproduced true to type in successive generations of asexual reproduction.

DETAILED DESCRIPTION OF THE VARIETY

Figure 1:
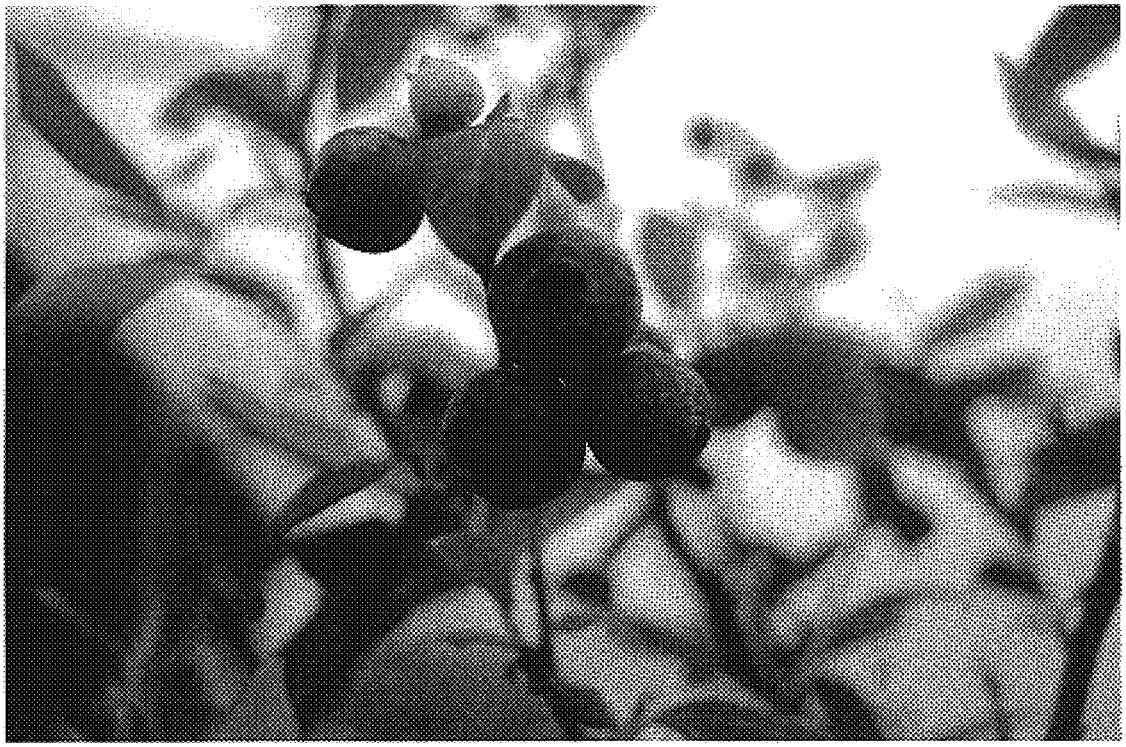
FIG. 1. Is a photographic illustration of the fruit and leaves of 'HX' including their shape, approximate color, arrangement in the cluster. Colors in the drawings are only approximate, in cases where the colors in the drawings differ from the RHS color designation given herein, the RHS designation should be considered and more accurate.
Figure 2:
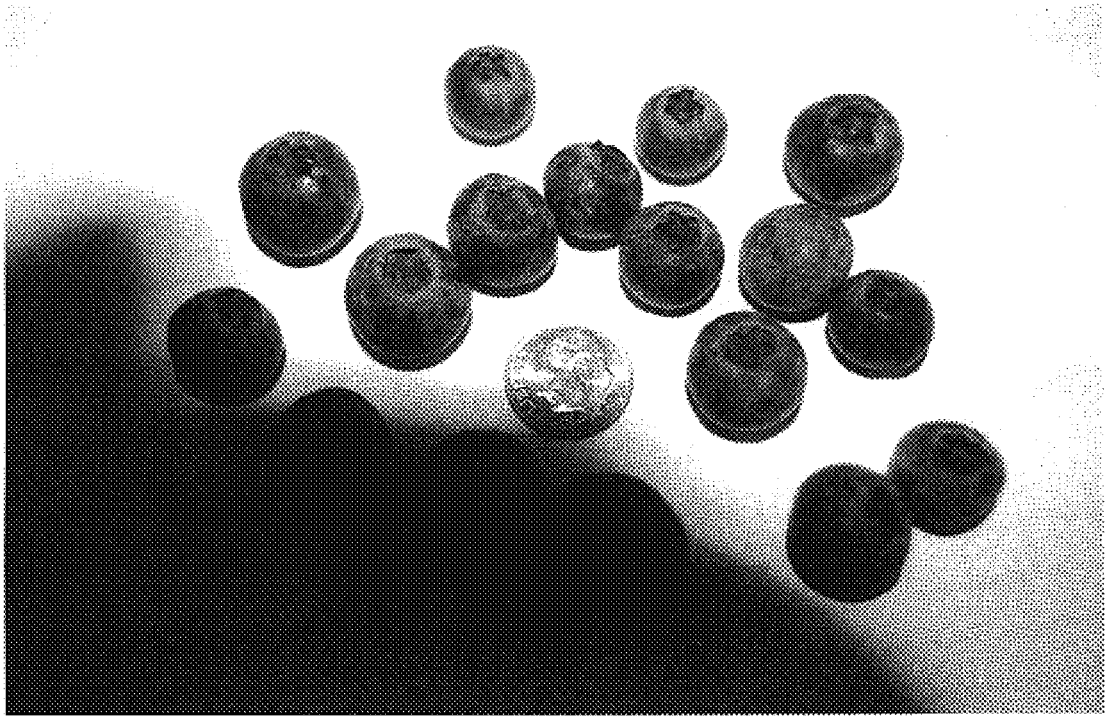
FIG. 2. Is a photographic illustration the whole fruit of 'HX', including the shape and color of the berries.
Figure 3:
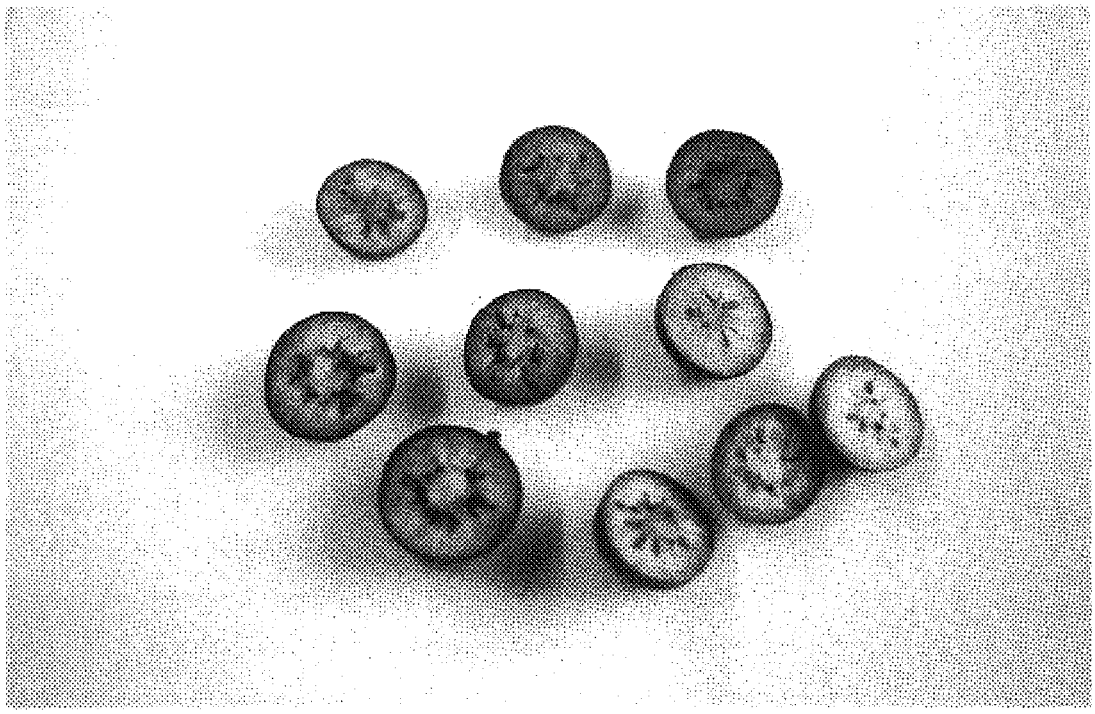
FIG. 3. Is a photographic illustration of slices of fruit was seeds from the plant 'HX' in Earleton, Fla.

The following is a detailed botanical description of the new and distinct variety of blueberry, its flower, fruit and foliage, based on observation of specimens grown at Earleton, Fla.

Bush: The following measurements were from mature plants eight years old.

Color description, except those given in common terms, use: designation cited from The Royal Horticulture Society (R.H.S.) Colour Chart. Where the color designation cited in R.H.S. charts differ from the color shown in the drawings the color cited from the R.H.S. charts should be considered accurate. Any deviation from those colors in the drawings is used to failure of the photographic process to exactly duplicate the colors of nature.

*Height of plants.*—4 to 5 feet.
*Trunk.*—Crown width slightly narrow 15"–18" wide.
*Suckering tendency.*—Medium.

Leaves:

*Leaf arrangement.*—Alternate, deciduous.
*Leaf length.*—3.5 cm.
*Leaf width.*—2.5 cm.
*Leaf shape.*—Elliptic lanceotlated.
*Leaf petiole.*—2 cm.
*Summer color of upper surface of leaves.*—Green (RHS 147A) and glabrous.
*Summer color of under surface of leaves.*—Pale gray (RHS 147B) and somewhat slightly pubescence.
*Autumn color of leaves.*—Orange (RHS 175A), yellowish green (RHS 144A) and reddish purple (RHS 187B).

Flowers: Flowers appear when foliage has 40% emergence.

Petals:

*Pollen color.*—(RHS 10D).
*Pollen production per flower.*—1.1 mg/flower/day to 2.1 mg.
*Flower type.*—Flower bracts are deciduous and glaucous. They appear when the foliage has 40% emergence. Flowers are borne on racemes that are longer than the pedicles.
*Flower corolla shape and size.*—Various width, 6–10 mm long and having a cylindrical-urn shaped.
*Corolla.*—The corolla begins as pinkish (RHS 62C), changing to pure white.
*Color of fresh anthers in flower at anthesis.*—(RHS 20A).
*Diameter of corolla tube at widest point.*—6–8 mm.
*Corolla shape and size.*—Corolla color at anthesis —(RHS 157D).
*Pedicel and peduncle color.*—(RHS 144C).
*Calyx color at anthesis* (*RHS 144 C*).—Number of calyx lobes — 5.
*Calyx surface.*—Protruding slightly 02.0 mm to 3.0 mm.
*Flower period.*—Appears when the foliage has 40% emergence in Earleton, Fla.
*Flower cluster.*—Medium.
*Number of flowers per cluster.*—5 to 8 mostly about 6.
*Berry cluster.*—Open.
*Pedicel length at berry maturity.*—5–8 mm, mostly 7 mm.
*Peduncle length at berry maturity.*—7 mm.
*Number of berries per cluster.*—Normally 6.
*Berry weight.*—0.9 to 1.4 grams per berry.
*Berry height.*—9–12 mm.
*Berry width.*—mm 12–17 mm.
*Berry skin color* (*ripe on plant*).—Light blue (RHS 98D).
*Berry skin color after bloom rubbed of.*—Very dark grayed purple (RHS N-186-A).
*Berry quality.*—Firm with small picking scar.
*Seed size.*—Well-developed seeds average 1.0 mm to 2.0 mm long times 0.7 mm to 1.3 mm wide.
*Color of mature seeds after drying.*—(RHS 164B).
*Internal flesh color of mature berry.*—Whitish gray (RHS 157C).
*Berry firmness 3.*—Scale 1–5.
*Berry flavor 4.*—Scale 1–5.
*Berry texture.*—Scale 1–10.
*Maturity date.*—March 2$^{nd}$ ripe 50% in Earleton, Fla. First commercial harvest (10% of the fruit ripe) typically Feb. 28$^{th}$ at Earleton, Fla. Last commercial harvest typically March 15$^{th}$ in Earleton, Fla.
*Productivity.*—Yields up to 16 pounds of berries per plant per year after 5.sup.th year.

Plant stems are cold hardy to minus 10 degrees F. (minus 23 degrees C). Fruit bracts are cold tolerating to 5 degrees F. (minus 15 degrees C.).

*Plant stem color.*—One and two year old stems are colored green (RHS 144B) and red (RHS 53B).
*Fruiting stems lateral color.*—Mostly yellow green (RHS 144D) with some being warty but glabrous.
*Color of branches.*—3 or more years — brown (RHS 177B).

The berries are suitable for fresh marketing but cannot be stored for long periods of time. Storage for 10 days at 35 degrees F. (1.5 degrees C.).

Plant stems are cold hardy to minus 10 degrees F. (mius 23° C.).

The following ratings are on a scale of 1–5, 5 is best.

a. spreading habit—5
b. upright—5
c. leaf fruit ratio—4
d. time to flower—early 5 is best for the climate where the cultivar is recommended
e. harvest—early 5 is best for the climate where this cultivar is recommended
f. fruit size—3
g. fruit color—4
h. fruit firmness—3
i. stem scar—4
j. tightness of cluster—5
k. foliar diseases—5
l. fruit rots—4
m. yield—4

Resistance to diseases, insects, and mites:

Phytophthora
Stem blight
Leaf spots
Bud mites

COMPARISON WITH SIMILAR VARIETIES

'HX' is most similar to Avonblue (non-patented), Misty (non-patented) and Sharpblue (non-patented). A comparison of 'HX' with those varieties is as shown below.

A. Misty characteristics:
1. Upright in growth habit 4 to 5 feet all, 2½ to 3 feet wide
2. Fruit quality.—3
3. Yield—4
4.Yield—4
5. Prune moderately yearly B. Avonblue characteristics.
1. Spreading outward growth slightly upright 3½ to 4½ feet tall, 3 to 3½ feet wide.
2. Fruit quality 2.5
3. Fruit size—2.
4. Yield—4
5. Needs aggressive pruning yearly.

C. Sharpblue characteristics.
1. Upright in growth 4 to 5½ feet and slightly spreading to 3 to 3½ feet wide.
2. Fruit quality—2
3. Fruit size—3
4. Yield—3
5. Prune moderately yearly.

D. Sensation characteristics.
1. Upright growth 4 to 5 feet tall 2½ to 3 feet wide.
2. Fruit quality—3.5
3. Fruit size—3
4. Yield—4
5. Prune moderately yearly on prune all growth after harvest to obtain a full crop the following season.

What is claimed is:

1. A new and distinct blueberry plant, substantially as illustrated and described, characterized by its free flowering without use of growth regulating chemicals, very low chilling requirement, very early fruiting, resistance by *phytophthora cinnamomii* and uniform ripening of its fruit.

* * * * *